(12) United States Patent
Faergemann et al.

(10) Patent No.: US 10,383,841 B2
(45) Date of Patent: Aug. 20, 2019

(54) ANTIMICROBIAL AND ANTIINFLAMMATORY COMPOSITION

(71) Applicant: Denovastella AB, Habo (SE)

(72) Inventors: Jan Faergemann, Gothenburg (SE); Thomas Hedner, Gallstad (SE); Olov Sterner, Malmo (SE); Lars Bjork, Skivarp (SE)

(73) Assignee: DeNovaStella AB, Habo (SE)

( * ) Notice: Subject to any disclaimer, the term of this patent is extended or adjusted under 35 U.S.C. 154(b) by 0 days.

(21) Appl. No.: 13/802,599

(22) Filed: Mar. 13, 2013

(65) Prior Publication Data

US 2013/0245112 A1    Sep. 19, 2013

Related U.S. Application Data

(60) Continuation of application No. 12/873,711, filed on Sep. 1, 2010, now abandoned, which is a division of application No. 11/994,252, filed as application No. PCT/SE2006/000802 on Jun. 30, 2006, now abandoned.

(60) Provisional application No. 60/696,695, filed on Jul. 5, 2005.

(30) Foreign Application Priority Data

Jul. 1, 2005   (SE) ...................... 0501530

(51) Int. Cl.

| | |
|---|---|
| *A61K 31/352* | (2006.01) |
| *A61K 8/02* | (2006.01) |
| *A61K 8/11* | (2006.01) |
| *A61K 8/49* | (2006.01) |
| *A61K 8/97* | (2017.01) |
| *A61K 36/28* | (2006.01) |
| *A61K 36/282* | (2006.01) |
| *A61Q 5/02* | (2006.01) |
| *A61Q 17/00* | (2006.01) |
| *A61Q 19/00* | (2006.01) |
| *A61Q 19/10* | (2006.01) |
| *A61K 31/047* | (2006.01) |
| *A61K 31/341* | (2006.01) |
| *A61K 31/343* | (2006.01) |
| *A61Q 5/00* | (2006.01) |

(52) U.S. Cl.
CPC .......... *A61K 31/352* (2013.01); *A61K 8/0208* (2013.01); *A61K 8/11* (2013.01); *A61K 8/498* (2013.01); *A61K 8/4973* (2013.01); *A61K 8/97* (2013.01); *A61K 31/047* (2013.01); *A61K 31/341* (2013.01); *A61K 31/343* (2013.01); *A61K 36/28* (2013.01); *A61K 36/282* (2013.01); *A61Q 5/02* (2013.01); *A61Q 17/005* (2013.01); *A61Q 19/00* (2013.01); *A61Q 19/10* (2013.01); *A61Q 5/006* (2013.01)

(58) Field of Classification Search
None
See application file for complete search history.

(56) References Cited

U.S. PATENT DOCUMENTS 5,369,129 A  *  11/1994  Swanbeck et al. ........... 514/738

FOREIGN PATENT DOCUMENTS

| WO | WO 02/41909 | 5/2002 |
|---|---|---|
| WO | WO 2004/41909 | 5/2002 |

OTHER PUBLICATIONS

Wang et al (Phytochemistry 28:2323-2327, 1989—abstract only).*
Aljancic et al (J Nat Prod 62:909-911, 1999).*
Stojanovic et al, J Enthopharmacology 101:185-190, 2005.*
Paediatr Child Health 5(8):477-482, 2000.*
Fugh-Berman (The 5-Minute Herb & Dietary Supplement Consult, p. 120, 2003).*
Abad et al. "The Activity of Flavonoids Extracted from *Tanacetum microphyllum* DC. (Composite) on Soybean Lipoxygenase and Prostaglandin Synthetase." Gen. Pharmac. vol. 26, No. 4. pp. 815-819. 1995.
Hethelyi et al. "Botanical and phytochemical study of *Artemisia abrotanum* (Southernwood) species." Olaj, Szappan, Kozmetika. vol. 54, No. 3. pp. 118-126. 2005.
Kotkar et al. "Antimicrobial and pesticidal activity of partially purified flavonoids of *Annona squamosa*." Pest. Manag. Sci. vol. 58. pp. 33-37. 2001.
Ramezani et al. "Chemical Composition and Antimicrobial Activity of the Volatile Oil of *Artemisia khorassanica* from Iran." Pharmaceutical Biology. vol. 42, No. 8. pp. 599-602. 2004.
Remberg et al., "Characteristics, clinical effect profile and tolerability of a nasal spray preparation of *Artemisia abrotanum* l. for allergic rhinitis", Phytomed 11:36-42, 2004.

* cited by examiner

*Primary Examiner* — Craig D Ricci
(74) *Attorney, Agent, or Firm* — Merchant & Gould P.C.

(57) ABSTRACT

The invention relates to the use of at least davanone and 1,8-cineol for the manufacture of an antimicrobial and/or antiinflammatory composition as well as a method of producing said composition.

7 Claims, No Drawings

ANTIMICROBIAL AND ANTIINFLAMMATORY COMPOSITION

This application is a Continuation of U.S. Ser. No. 12/873,711, filed 1 Sep. 2010 which is a Divisional of U.S. Ser. No. 11/994,252, filed 8 May 2008 which is a National Stage Application of PCT/SE2006/000802, filed 30 Jun. 2006, which claims benefit of Serial No. 0501530-0, filed 1 Jul. 2005 in Sweden and U.S. Ser. No. 60/696,695, filed 5 Jul. 2005 and which applications are incorporated herein by reference. To the extent appropriate, a claim of priority is made to each of the above disclosed applications.

FIELD OF INVENTION

The invention relates to the use of at least davanone and 1,8-cineol for the manufacture of an antimicrobial and/or antiinflammatory composition as well as a method to produce said composition.

BACKGROUND OF THE INVENTION

Pathogenic microorganisms may be combated in different ways depending on if the purpose is to prevent growth, inhibit further growth, or reduce or eliminate the microorganism. In addition, the approach may be different depending on where the microorganism is located, such as on a surface (e.g. skin or mucous membrane), in a liquid (e.g. sweat, saliva), on or within the mammalian body. In addition, any preparation used for antimicrobial and anti-inflammatory purposes, should be non-toxic, non- or low-allergenic, environmentally friendly and possible to produce at low cost. A microbial infection also causes inflammation of the infected area. Microorganisms, which are resistant or even multi-resistant against conventional antibiotics, are becoming more and more common worldwide and there is a concern about the proper use of such antibiotics. The present invention is thereby focused on developing alternatives to the compositions available on the market today, to be used to combat microbes and/or reduce inflammation.

SUMMARY OF THE INVENTION

The object of the invention is to provide a new antimicrobial and/or antiinflammatory composition, which can be used to combat microorganisms as well as treating inflammation, wherein the composition due to the presence of terpene(s) can reach microorganisms even within the skin or mucosa.

In a first aspect the invention relates to the use of at least davanone and 1,8-cineol for the manufacture of an antimicrobial and/or anti-inflammatory composition. By the use of davanone and 1,8-cineol from for example one or more plants a unique composition is obtained, wherein a synergistic effect between the terpenes are obtained and an increased antimicrobial effect obtained compared to when the terpenes are used alone. Due to the presence of the terpene content the composition may even reach micororganisms present within the mucosa or skin.

In a second aspect the invention relates to A method of extracting antimicrobial and/or anti-inflammatory components from one or more plants comprising the steps of; providing at least one plant material, processing said plant material by distillation and obtaining a water and an oil part, wherein said water part comprises the green plant material and obtaining an oil part comprising at least davanone and/or 1,8-cineol In a third aspect the invention relates to a method in which said antimicrobial and/or antiinflammatory composition is used to treat a mammal such as a human being or an animal.

Further advantages and objects with the present invention will be described in more detail below.

DETAILED DESCRIPTION OF THE INVENTION

Plant Extract

According to a first aspect, the invention relates to the use of davanone and 1,8-cineol for the manufacture of an antimicrobial and/or antiinflammatory composition, wherein said composition provides an alternative treatment to already known and commercially available compositions, such as for the treatment of bacteria which are resistant to commercially available antibiotics as well as for the treatment of mammals which are allergic to known medicaments. While davanone and 1,8-cineol have some antimicrobial effect it has surprisingly been found that the effect may be increased through the synergistic effects between the terpenes. Additionally the composition may comprise flavonols, which also shows antimicrobial and/or anti-inflammatory effects to increase the total effect of the composition. Davanone, 1,8-cineol as well as flavonols may be isolated/extracted/purified from one and the same plant species or from different ones. If the different components (davanone, 1,8-cineol and flavonols) are extracted from different plant species they may be mixed after being extracted. The different components may under certain conditions also be extracted together. Examples of plants from which the components may be obtained are *Artemisia* species, *Lantana camara* or *Tanacetum* species, such as *Tanacetum vulgare*. The content of the tepenes may be from about 0.0025 to about 1.0% (w/v) and the content of the flavonols from about 0.1 to about 100 ug/ml. Said flavonol may be selected from the group comprising casticin, centaureidin, quercetin 3.4-dimethyl ether and quercetin 3.7-dimethyl ether. In a specific embodiment the flavonols are casticin, centaureidin, quercetin 3.4-dimethyl ether and quercetin 3.7-dimethyl ether. In that specific embodiment the amount of the flavonols are from about 0.4 to about 400 ug/ml of the four flavonols, such as from about 0.1 to about 100 ug/ml of casticin, such as 0.2, 1, 10, 20, 30, 40, 50, 60, 70, 80 or 90 ug/ml, from about 0.1 to about 100 ug/ml of centaureidin, such as 0.2, 1, 10, 20, 30, 40, 50, 60, 70, 80 or 90 ug/ml, from about 0.1 to about 100 ug/ml of quercetin 3.4-dimethyl ether, such as from 0.2, 1, 10, 20, 30, 40, 50, 60, 70, 80 or 90 ug/ml and from about 0.1 to about 100 ug/ml of quercetin, such as from 0.2, 1, 10, 20, 30, 40, 50, 60, 70, 80 or 90 ug/ml.

The components, 1,8-cineol and davanone may be present in an amount of 5-100%, such as 10, 15, 20, 25, 30, 35, 40, 45, 50, 55, 60, 5, 70, 75, 80, 85, 90 or 95% of the total terpene content within the composition. The plant extract may also contain terpenoids as well as coumarins.

The plant extract may be extracted/obtained/purified from *A. oelandicum, A. dracunculus, A. campestris, A. vulgaris, A. absinthium, A. stelleriana, A. rupestris A. abrotanum, A. pallens, A. lerchiana, Tanacetum corymbosum, A. maritima, A. thuscula, A. rehan, A. persica, A. glabella, Lantana camara* and *Tanacetum vulgare*.

The amount of the different flavonols differs between the different plant species and is dependent on the growth conditions, such as soil, growth length, temperature etc. As one example 100 g dry plant material of the entire plant southernwood, without the root, contains the following flavonols: casticin (approximately 7 mg) centaureidin (approximately 5 mg) quercitin 3.4'-dimethyl ether (approximately 5 mg) quercetin 3.7-dimethyl ether (approximately 5 mg).

Flavonols represent a group of well-defined so-called secondary metabolites, which are found in most plants. The flavonols show variations in the number of hydroxyl groups and in the degree of methylation. In plants, flavonols are bound to sugar molecules. However, during the method used to extract the flavonols, the flavonols are released by hydrolysis of the flavonol glycosides.

It has surprisingly been found that the plant extract of the invention has a rapid onset and prolonged antimicrobial as well as anti-inflammatory effect. Importantly, the antimicrobial effects can be obtained already within hours or days. The therapeutic effect remains for a considerable period of time after the preparation has been administered. Additionally, such a composition is an alternative to the compositions, which are used today. It may be used to combat microorganisms, which are resistant to the compositions used today. Additionally it may be used as an alternative for mammals, which are allergic to other compositions. The use of a plant extract may also reduce the costs of production of the agent.

Cultivation of the Plant Material and Preparation of the Plant Extract

Research and fieldwork has demonstrated that the procedures of harvesting and handling of the plants and plant material such as *Artemisia* plants and the manufacture of the preparation are essential to its biological activity. This also implies that the antimicrobial and anti-inflammatory properties of the invented extract may be different from time to time. However, the process to be used depends on the cultivation system. Previously it has been common procedure when using for example *Artemisia* or *Tanacetum* plants that the harvested material has been dried, and that the extract is prepared from the dried plant material. This is far from optimal when aiming to produce an antimicrobial or anti-inflammatory composition, when larger amount are to be processed. One example how to grow the plant material is for example to grow an *Artemisia* plant, in the Scandinavian or other Northern hemisphere climate in open fields and make the extract from relatively young, fresh plants harvested during May-July. With a later harvest the plant grows woody, and it becomes difficult to provide an optimal extract in an easy way. This is due to the fact that the content of anti-microbial and anti-inflammatory essential oils in the green mass of fresh plants is higher than that of dried plants, and that the composition of different essential oils/etheric oils in the fresh green mass is different from that of more woody plants. During the course of the growth of the plant there is a gradual change of the essential oil/etheric oil fraction, which at a late harvest becomes unfavourable for the purposes of the invention. While the total content of essential oils/etheric oils is relatively constant, the content of the valuable oil component davanone decreases whereas the content of 1,8-cineol increases. One example how the plants may be grown is in green houses under controlled conditions, well known for a person skilled in the art. Alternatively, different in vitro methods such as fermentation techniques may be used as long as it is possible to obtain a plant extract comprising the above mentioned components in specific amounts.

A further problem in producing the plant extract is that many *Artemisia* species, e.g. southernwood, cannot be propagated by seeds so that the propagation has to be done vegetatively, such as by cutting breeding, protoplasts or other in vitro techniques. This gives, however, the advantage that the grown material becomes a clone of a so called chemotype, having a defined chemical composition. A special clone "tycho" was developed from material found on the island Ven in Sweden used in the clinical tests.

One example of a process to be used for the preparation of the plant extract follows below;

Step 1. Fresh southernwood or tansy, preferably harvested in June or July (in Scandinavian climate) is processed by distillation, such as steam distillation. The steam is produced through boiling the plant material with water or produced through an external source and led through the biomass.

Step 2. Water steam and oils are allowed to condense, whereby the etheric oils present in the oil part comprising the terpenes, become separated and are collected for later use.

Step 3. The pre-cooked water part comprising the green plant material also called the green mass of step 1 is boiled in water or heated by steam for 5-60 minutes. By such cooking the composition is changed chemically, and the flavonol glycosides, which are present in the plant are hydrolyzed to free flavonols and sugar.

Step 4. The green mass is dried, and thereafter extracted with alcohol, such as ethanol. How to perform such an extraction is well-known for a person skilled in the art. The free flavonols are dissolved in the alcoholic extract. Alternatively, the flavonols are extracted with the essential oils obtained in step 2.

Step 5. In this step the essential oils, which were separated and collected in step 2, are admixed into the alcoholic extract from step 4.

Step 6. The mixture of the etheric oil comprising at least davanone and/or 1,8-cineol from step 2 and the alcoholic extract from step 4 are diluted in water to an alcohol content of about 25%, whereby a final product is obtained. A lower alcohol content reduces the solubility of the oil whereas a higher alcohol content may be too irritating to the patient's mucosa, skin and other tissues to which the preparation may be applied.

Step 7. The product from step 6 is further processed to provide a suitable preparation for e.g. topical use and then packed in a suitable package, for instance a spray container in order to make it possible to spray the preparation into the nose or the throat, use it in eye drops or apply it topically to the skin, mucous membranes or teeth, in a cream, ointment, solution, paste, gel or alternatively for use as an additive in food products or other products.

However, the preparation process to obtain the plant extract can be performed in different ways, and one example is by using the method described in WO 02/41909. In one embodiment the davanone is obtained from one plant, 1,8-cineol from another one and the flavonols obtained from a third plant and the components are then mixed with each other. By such an approach it is possible to obtain different mixtures with different content of the davanone and/or 1,8-cineol and/or flavonols, since different plant species contains different amount of the different components and some plant species contains solely one or two of the components.

Pharmaceutical Composition

The invention also relates to a pharmaceutical composition comprising the above defined antimicrobial or antiinflammatory extract, which further may include a pharmaceutically acceptable salt, diluent, excipient, carrier, preservative, stabiliser or adjuvants.

Pharmaceutical compositions according to the invention are typically administered in a composition that includes one or more pharmaceutically acceptable, adjuvants, diluents, carriers or excipients. Such pharmaceutical compositions may be prepared in a manner known in the art that is sufficiently storage stable and suitable for administration to humans and animals.

"Pharmaceutically acceptable" means a carrier, diluent, adjuvant or excipient that at the dosage and concentrations employed does not cause any unwanted effects in the patients to whom it is administered. Such pharmaceutically acceptable carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The pharmaceutical composition may be admixed with adjuvants and formulated into a suitable formulation for topical administration. Other adjuvants and modes of administration are well known in the pharmaceutical art.

The pharmaceutical compositions may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

The pharmaceutical composition according to the invention may be processed into and packed as a composition for local or topical administration for use on skin, on mucous membranes, in eyes, in ears, on teeth, gumsa, finger and toe nails, hair or is used as an additive in other medicinal or cosmetic products. Suitable pharmaceutical preparation forms are, ointments, creams, lotions, gels, solution, shampoos, dermal or mucosal patch, sachet or wafers, emulsions, powder, suspensions, and also preparations with protracted release of active compounds, in whose preparation excipients, diluents, adjuvants or carriers are customarily used as described above.

The pharmaceutical composition will be administered to a patient in a pharmaceutically effective dose. By "pharmaceutically effective dose" is meant a dose that is sufficient to produce the desired effects in relation to the condition for which it is administered. The exact dose is dependent on the activity of the compound, manner of administration, nature and severity of the disorder, age and body weight of the patient different doses may be needed. The administration of the dose can be carried out both by single administration in the form of an individual dose unit or else several smaller dose units and also by multiple administration of subdivided doses at specific intervals.

The pharmaceutical composition of the invention may be administered alone or in combination with other therapeutic agents. These agents may be incorporated as part of the same pharmaceutical composition or may be administered separately.

The "patient" for the purposes of the present invention includes both humans and other mammals. Thus the methods are applicable to both human therapy and veterinary applications.

Method of Treatment

The invented composition comprising the above defined plant extract and compositions comprising said plant extract can efficiently be used for the treatment of topical infections caused by virus, bacteria or fungi or prevention of inflammatory symptoms associated with such infectious agents or related to other pathological conditions.

Examples of conditions where the antimicrobial composition according to the present invention may be therapeutically advantageous is for example, but not limited to cold sores, herpes simplex infections, impetigo, tinea pedis, dandruff, acne, eczema, atopic dermatitis, psoriasis, other types of eczema or fungal skin or mucous membrane infections.

Additionally, the antimicrobial effects of the invented composition have been demonstrated against both sensitive and multi-resistant gram-positive and gram-negative bacteria, common viruses such as the Herpes Simplex virus as well as common pathogenic fungi such as *Candida albicans*, *Trichophyton rubrum* and several *Malazzesia* species, such as *M. globosa, M. sympodialis* and *M. obtusa*. Accordingly, the composition has shown good effect against multi-resistant bacteria, which makes the preparation useful as an alternative for topical antimicrobial therapy in humans and animals. Specific examples of diseases, which can be treated are herpes labialis, impetigo, tinea pedis, and dandruff. The composition may be a cream, such as for the patients with impetigo; a shampoo or solution, such as in patients with dandruff or a gel or a cream, such as in patients with herpes labialis or tinea pedis. Additionally the composition may be used in the therapeutic as well as prophylactic management of the above mentioned different conditions.

EXAMPLES

Example 1

Extracts

Extracts were acquired from Olov Sterner, Department of Organic and Bioorganic Chemistry, Lund University, Sweden. Conventional methods were used to produce one essential oil and one ethanol extract from the plant material (called DNS extracts). In the first study a 2.5% ethanol extract was used (25 g plant material per 1000 ml ethanol). In a second study, an extraction with tenfold the concentration was used (25%, 250 g plant material per 1000 ml ethanol) in order to reduce the effect of ethanol. The oil contained mainly 1,8-cineole and davanone. In addition, the terpenoids 1,8-cineole and davanone were tested as pure compounds. It is interesting that a mixture of davanone and 1,8-cineol are more effective than the terpenes alone. The extracts were prepared according to the method disclosed in WO 02/41909.

A second set of following extracts was prepared using the above defined method.
1. Pure davanone
2. Pure cineol
3. Southern wood oil with a low amount of davanone/cineol
4. Southernwood oil with a high amount of davanone/cineol
5. Cineol oil with flavonols were the flavonols were extracted with the cineol
6. Southernwood oil with flavonols were the flavonols were extracted with the cineol
7. Flavonols extracted with ethanol. 10 g dry souther wood/100 ml ethanol
8. Concentrated flavonols. 40 g dry souther wood/100 ml ethanol The southernwood oils were prepared through steam distillation. Pure davanone was prepared from *Artemisia pallens* and Cineol was prepared from *Eucalyptus globulus*.

Bacteria and Fungi

The five strains of *Malassezia* were CBS7019 *M. Furfur*, CBS 1871 *M. Pachydermatis*, CBS7956 *M. Slooffiae*, CBS7966 *M. Globosa* and 42132 *M. Sympodialis*. The *Staphylococcus aureus* strain and *Candida albicans* H29 strain (grown on mycobiotic plates). *Malassezias* were cultured on PO plates and kept in room temperature. *Candida albicans* were grown on mycobiotic plates at room temperature. Preceding the first experiment the yeasts were reinoculated and stored for five days in a 32° C. thermostat. Afterwards they were continually reinoculated every week to ensure viable strains. *S. aureus* were refrigerated and reinoculated on a horse blood plate and incubated for one day in 37° C. before being included in any study.

Test Agar

DST-TG-agar (diagnostic sensitivity test agar) with a glycerol monostearate and tween content to meet the growth requirements of the *Malassezias* was used. Unlike e.g., Seborrauds agar DST—agar does not inhibit growth and is therefore preferred here. The agar was obtained from the Microbiological Laboratories, Sahlgrenska, Gothenburg, Sweden. When received the agar was in a liquid form requiring storage at 55° C.

Agar Dilution Method

The oil extract from example 1 were diluted in DMF (dimethyl formamide) producing a stock solution with 20% extract and 80% DMF. A secondary stock solution was made by diluting a decided volume of the first stem solution in PBS. Finally the solutions were mixed with the soluble agar to obtain concentrations of the extract of 1, 0.5, 0.25, 0.125, 0.0625, 0.05, 0.025 and 0.0125% in the agar. Since the ethanol extract readily dissolved with the agar no emulsifier was needed. The ethanol extract was diluted directly with the agar to obtain concentrations of the extraxt of 1, 0.5, 0.125, 0.1, 0.05, 0.0125, 0.01 and 0.005% in the agar. No precipitations or supernatants were observed.

Microbes were harvested and suspended into PBS and manually counted in Barker chambers to receive concentrations of $10^7$ cells/ml for the *Malassezias* and $10^5$ cells/ml for the *Staphylococci* and *Candida*. Due to poor growth of *M. globosa*, *M. slooffiae* and emulsions were modified to contain $10^8$ cells/ml in the third experiment.

Using a Pasteur micropipette, plates were inoculated with 20 μl of emulsion. Plates were inoculated with either three or four microorganisms. Control plates containing only agar and plates with mirrored concentration series of DMF and ethanol were made. Additionally, all plates had paralleled controls.

Plates were incubated in 37° C. for approximately 3 days and then read.

We found that the studied substances inhibited the growth of all microorganisms. The ethanol extract included in the first study exhibited the lowest MICs (ranging from 0.0125-0.025%) (FIG. 1). Davanone was essentially the most potent antimicrobial agent of the essential oil (MIC spread: 0.0125-0.125%). The extract from example 1 was however twice as efficient against *S. aureus* (0.0625%). Initially, 1,8-cineole was similar in potency to the extract obtained from example 1. In the subsequent experiment nearly all MICs were four times the value (0.5%). Contrary to previous experiences *M. globosa* obtained the highest MIC (1.0%). Neither the ethanol controls, nor the DMF had lower MICs than the terpene substances. (Aligned concentrations of DMF and ethanol in comparison to concentrations of substances are shown in table 1:3). The overall most resistant microorganisms were the *Staphylococcus*, *M. globosa* and *M. slooffiae* were the least pertinacious microorganisms. *C. albicans* was slightly less sensitive than *M. furfur*. The highest attained MIC of studied substances was 0.5% (of cineole) and the lowest 0.0125% (ethanol extract 0.25%). It is interesting that a mixture of davanone and 1,8-cineol are more effective than the terpenes alone. It is also interesting that the flavonols extracted by the etheric oils give an antimicrobial affect of the same magnitude as the flavonols extracted by the alcohol.

The results are shown in Table 1-3.

TABLE 1

| Experiment I | Microorganisms | | | | | | | |
|---|---|---|---|---|---|---|---|---|
| Substance | *M. furfur* | *M. sympodialis* | *M. pachydermatis* | *M. slooffiae* | *M. globosa* | *C. albicans* | *S. aureus* | |
| DNS in ethanol 0.25% | 0.0125% | 0.0125% | no growth | no growth | no growth | 0.0125% | 0.025% | |
| DNS in oil 25% | 0.0625% | 0.0250% | no growth | no growth | no growth | 0.125% | 0.0625% | |
| DMF | 2.500% | 2.500% | no growth | no growth | no growth | 5.000% | — | (maximum titre: 5.0%) |
| No substance (agar control) | Growth | growth | no growth | no growth | no growth | growth | growth | |

TABLE 2

| Experiment II Substance | *M. furfur* | *M. sympodialis* | *M. pachydermatis* | *M. slooffiae* | *M. globosa* | *C. albicans* | *S. aureus* | |
|---|---|---|---|---|---|---|---|---|
| Cineole | 0.125% | 0.0625% | 0.125% | 0.125% | 0.125% | 0.125% | — | (maximum titre: 0.125%) |
| Davanone | 0.0625% | 0.0125% | 0.0625% | 0.0125% | 0.025% | 0.0625% | 0.125% | |
| DNS in ethanol 2.5% | — | — | — | 0.025% | 0.025% | — | — | (maximum titre: 0.025%) |
| DMF | 5.000% | 2.500% | 5.000% | 1.250% | no growth | 5.000% | 10.000% | (minimum titre: 0.3125%) |
| Ethanol control | — | — | — | — | — | — | — | (maximum titre: 0.960%) |
| No substance (agar control) | growth | growth | Growth | poor growth | poor growth | Growth | Growth | |

TABLE 3

| Experiment III Substance | M. furfur | M. sympodialis | M. pachydermatis | M. slooffiae | M. globosa | C. albicans | S. aureus |
|---|---|---|---|---|---|---|---|
| Cineole | 0.500% | 0.500% | 0.500% | 0.500% | 1.000% | 0.500% | 0.500% |
| DNS in ethanol 2.5% | 0.200% | 0.200% | 0.200% | 0.200% | 0.200% | 0.200% | 0.200% |
| No substance (agar control) | growth | growth | growth | growth | growth | growth | growth |

In the following examples three different extracts were used: F1, a concentrated ethanol extract containing approximately 20 ug/ml Casticin, 15 ug/ml centaureidin, 20 ug/ml quercetin 3.4-dimetyl-ether and 20 ug/ml quercetin 3.7-dimethyl-ether; extract F2, which is the extract F1 diluted 1:4 with water; extract F3, which is the extract F1 diluted 1:10 with ethanol.

Example 2

Male, 45 years old, physician. The patient suffers from recurrent labial herpes simplex. The patient was treated by the extract F1, described above at an early phase of the labial infection. The preparation contained 0, 1 ml essential oil per 20 ml alcohol. Development of herpes crusts was aborted.

Example 3

The same patient used a preparation for prophylaxis when symptoms were just noticeable, extract F1 containing 0.2 ml essential oil per 20 ml alcohol. Full effect was obtained within 2 doses, and development of labial herpes was aborted.

Example 4

A female, 35 years old, with tinea pedis. A gel was used containing 0.1 ml essential oil per 20 ml alcohol, extract F1. The patient became free of the fungal infection within 1 day and free of local symptoms within 2 days.

Example 5

Another patient, a 12 year old boy with impetigo due to Staphylococcus aureus was treated with a gel according to the invention containing 0.1 ml essential oil per 20 ml alcohol of extract F2. The bacterial infection was successfully treated, the local eruptions healed within 2 weeks and symptoms were reduced.

Example 6

A 55 year old male with recurrent dandruff was treated with a shampoo once daily followed by a lotion according to the invention containing 0.1 ml essential oil per 20 ml alcohol of extract F3. The dandruff was successfully treated within 5 days and the dermatitis reaction of the scalp was significantly improved during the same time interval.

Example 7

A male engineer, 44 years old used a topical gel for a pityriasis versicolor infection. The fungal infection was successfully treated and dermatological reactions were improved within one week.

Example 8

A female nurse, 54 years old used a shampoo and a topical solution in the scalp for dandruff. The condition was successfully treated and the dandruff disappeared within 2 weeks of use.

The above examples thus show that the highest amount of oil should not be higher than 0.2 ml per 20 ml of the product, and that the lowest value should not be less than 0.0005 ml per 20 ml of the product.

In patients with infectious inflammation of the skin or the mucous membranes, such as sores on the lip, dandruff and inflammation of the scalp, impetigo, or athlete's foot (tinea pedis), or other inflammations such as gingivitis, substantial symptom relief occurred and the infection disappeared within days. There were no adverse effects noted while using the preparation.

Example 9

Different suitable products.
Gel

| Ingredients | INCI | % |
|---|---|---|
| Water | Aqua | qs |
| Pentane-1,5-diol | pentan-1,5-diol | 1-10 |
| Etheric oil | "A. Abrotanum" | 0.05-0.5 |
| Mulsifan RT 141 | Polysorbate 20 | 2.00 |
| SYNTHALEN K | Carbomer | 1.50 |
| NaOH (18% solution) | Sodium hydroxide | 2.3 × 0.18 = 0.41 |
| Perfume | Perfume | 0.20 |
| Sharomix (preservative) | Phenoxyethanol, Methylparaben, Ethylparaben Propylparaben | 0.60 |

Creme

| % | Ingred. | INCI | app % |
|---|---|---|---|
| 77.89 | Water | Aqua 100% | qs |
|  | pentan-1,5-diol |  | 1-10% |
| 0.05-0.5 | A. abrotanum oil |  | 0.05-0.5 |
| 3.50 | Squalane | Squalane 100% | 3.00 |
|  | Veg oil |  | app 5.00 |
| 3.00 | Betacyklodextrin | Cyclodextrin 100% | 3.00 |
| 3.00 | Silosoft PEDM | Phenethyl dimethicone | 3.00 |
| 3.00 | M.O.D. | Octyldodecyl myristate | 3.00 |
| 2.50 | Oxetal 365 | PEG-11 avocado glycerides | 2.50 |
| 3.50 | Emulium delta | *Cetyl alcohol 25-50% | 1.50-3.00 |
|  | Emulium delta | *Glyceryl stearate 25-50% | 1.50-3.00 |
| 2.50 | Hyfatol CS | Cetearyl alcohol | 2.50 |
|  | Emulium delta | *PEG-75 stearate 10-24.9% | 0.60-1.49 |
| 0.30 | Satiaxane | Xanthan gum | 0.30 |
|  | Emulium delta | *Ceteth-20 5-9.9% | 0.30-0.59 |
|  | Emulium delta | *Stereth-20 5-9.9% | 0.30-0.59 |
| 0.02 | NaOH | Sodium hydroxide | 0.016 |
| 0.15 | Parfume | Parfum | 0.15 |

-continued

| %    | Ingred.    | INCI                                          | app % |
|------|------------|-----------------------------------------------|-------|
| 0.08 | Ultrez 21  | Acrylates/C10-30 alkyl acrylate crosspolymer  | 0.08  |
| 0.50 | Sharomix   | Phenoxyethanol Methylparaben Ethylparaben Propylparaben | |
| 0.01 | Lactic acid | Lactic acid. adj. to pH 5.5 (app. 0.01%).    |       |

Schampo

| Water | qs | Aqua |
|-------|-----|------|
| Lumorol K5240 | 0.66 × 23.91% > 15.78 | Sodium laureth sulphate |
| Amfotensid B4 | 0.3 × 6.35 = 1.91 | Cocamidopropyl betaine |
| Lumorol | 23.91 × (3.3-6.6) 0.79-1.58 | |
| MP | 4.00 × 0.11 = 0.44 | |
|  | ❑3.93. | |
| A. abrotanum extract | | |
| Lumorol | 23.91 × (0.66-3.3) 0.158-0.789 | Disodium laureth sulfosuccinate |
| Lumorol | 23.91 × (0.66-3.3) 0.158-0.789 | PEG-9 cocoglycerides |
| MacPearl | (4.00%) 4.00 × 0.17 = 0.68 | Glycol distearate |
| NaCl(amphotensid) | 6.35 × 0.05 = 0.318 | Sodium chloride |
| MP | 4.00 × 0.07 = 0.28 | Lauramide DEA |
| Perfume | 0.35 | Perfume |
| Sharomix | 0.60 | |
| Phenoxyethanol | 70-75% | |
| Methyl paraben | 15-17% | |
| Ethyl paraben | 3.6-4.4% | |
| Propyl paraben | 7.5-8.5% | |

The invention claimed is:

1. A method of treating tinea pedis in a subject in need thereof, comprising:
administering to the subject having tinea pedis a composition comprising:
0.0025 to 1.0% (w/v) of a combination of davanone and 1,8 cineol;
0.1 to 100 .mu.g/ml casticin;
0.1 to 100 .mu.g/ml centaureidin;
0.1 to 100 .mu.g/ml quercetin 3,4-dimethyl ether;
0.1 to 100 .mu.g/ml quercetin 3,7-dimethyl ether; and
1 to 10% pentane-1,5-diol.

2. The method of claim 1, wherein the composition is in the form of a gel, spray, shampoo, or cream.

3. The method of claim 1, wherein the composition is in the form of a cream.

4. The method of claim 1, wherein the davanone and 1,8-cineol are from one or more plants selected from the group consisting of *A. oelandicum, A. dracunculus, A. campestris, A. vulgaris, A. absinthium, A. stelleriana, A. rupestris, A. abrotanum, A. pallens, A. lerchiana, A. thuscula, A. rehan, A. persica, A. glabella, Lantana camara* and *Tanacetum vulgare*.

5. The method of claim 3, wherein the davanone is from *A. pallens*, the 1,8-cineol is from *Eucalyptus globulus*, and the flavonols are from *A. abrotanum*.

6. The method of claim 3, wherein the davanone and 1,8-cineol are from *A. abrotanum*.

7. A method of treating tinea pedis in a subject in need thereof, comprising:
administering to the subject having tinea pedis a gel composition comprising:
0.0025 to 1.0% (w/v) of a combination of davanone and 1,8 cineol;
0.1 to 100 .mu.g/ml casticin;
0.1 to 100 .mu.g/ml centaureidin;
0.1 to 100 .mu.g/ml quercetin 3,4-dimethyl ether;
0.1 to 100 .mu.g/ml quercetin 3,7-dimethyl ether; and
1 to 10% pentane-1,5-diol.

* * * * *